United States Patent
Will et al.

(10) Patent No.: US 11,257,571 B2
(45) Date of Patent: Feb. 22, 2022

(54) IDENTIFYING IMPLIED CRITERIA IN CLINICAL TRIALS USING MACHINE LEARNING TECHNIQUES

(71) Applicant: International Business Machines Corporation, Armonk, NY (US)

(72) Inventors: Eric W Will, Rochester, MN (US);
Adam Clark, Rochester, MN (US);
Lisa Wellman, Rochester, MN (US);
Janice R Glowacki, Rochester, MN (US)

(73) Assignee: International Business Machines Corporation, Armonk, NY (US)

(*) Notice: Subject to any disclaimer, the term of this patent is extended or adjusted under 35 U.S.C. 154(b) by 276 days.

(21) Appl. No.: 16/267,715

(22) Filed: Feb. 5, 2019

(65) Prior Publication Data
US 2020/0251188 A1 Aug. 6, 2020

(51) Int. Cl.
*G16H 10/20* (2018.01)
*G16H 10/60* (2018.01)

(52) U.S. Cl.
CPC .......... *G16H 10/20* (2018.01); *G16H 10/60* (2018.01)

(58) Field of Classification Search
CPC .............................. G16H 10/20; G16H 10/60
USPC .......................................................... 705/3
See application file for complete search history.

(56) References Cited

U.S. PATENT DOCUMENTS

| | | |
|---|---|---|
| 7,194,301 B2 | 3/2007 | Jenkins et al. |
| 8,202,095 B2 | 6/2012 | Shankle et al. |
| 2002/0077853 A1* | 6/2002 | Boru .................. G16H 10/20 705/2 |
| 2005/0234740 A1* | 10/2005 | Krishnan ......... G06Q 10/06398 705/2 |
| 2008/0195326 A1* | 8/2008 | Munzer ................ G16B 50/00 702/20 |
| 2013/0332191 A1* | 12/2013 | Hoffman ............ G16H 10/20 705/3 |
| 2016/0314280 A1* | 10/2016 | Fusari ................. G16H 10/60 |

(Continued)

OTHER PUBLICATIONS

Mapstone, James, Diana DE Elbourne, and Ian G. Roberts. "Strategies to improve recruitment to research studies." Cochrane Database of Systematic Reviews 3 (2002). (Year: 2002).*

(Continued)

*Primary Examiner* — Michael Tomaszewski
*Assistant Examiner* — Rachael Sojin Stone
(74) *Attorney, Agent, or Firm* — Patterson + Sheridan, LLP

(57) ABSTRACT

A method and apparatus for identifying implied criteria for a clinical trial is disclosed. An example method generally includes generating a training data set from a corpus of clinical trial specifications. The training data set may include at least a first sample corresponding to a first trial. The first sample may include a first feature based on one or more explicitly stated trial criteria, a second feature based on metadata describing the first trial, and a third feature based on patient data of patients associated with the first trial. A machine learning model is trained, using a supervised learning approach, based on the training data set. A system processes a second trial as an input to the trained machine learning model to determine one or more implied criteria that are not explicitly enumerated in a specification for the second trial.

20 Claims, 4 Drawing Sheets

(56) References Cited

U.S. PATENT DOCUMENTS

2019/0311787 A1* 10/2019 Graiver .............. G16H 10/60
2021/0358576 A1* 11/2021 Vrouwenvelder ... G08G 1/0141

OTHER PUBLICATIONS

Papernot, N. et al, "Semi-Supervised Knowledge Transfer for Deep Learning from Private Training Data," 2017. 16 pages.

Deng, Y. et al, "The Generation of a Corpus for Clinical Sentiment Analysis," 2016, 14 pages.

Authors et. al.: IBM, "Patient Targeting Methodology for Healthcare,"Original Publication Date: Aug. 23, 2005 | IP.com No. IPCOM000127331D | IP.com Electronic Publication Date: Aug. 23, 2005 | 3 pages.

Authors et. al.: Disclosed Anonymously, "Method for Efficiently Selecting Patients for Clinical Trials," IP.com No. IPCOM000232370D | IP.com Electronic Publication Date: Nov. 4, 2013 | 3 PAGES.

Authors et. al.: Disclosed Anonymously, "Extensible Method for Criteria-Driven Answer Scoring in a Deep Question Answering System," IP.com No. IPCOM000239037D | IP.com Electronic Publication Date: Oct. 2, 2014 | 5 PAGES.

* cited by examiner

IDENTIFYING IMPLIED CRITERIA IN CLINICAL TRIALS USING MACHINE LEARNING TECHNIQUES

BACKGROUND

The present invention relates to using machine learning techniques in clinical trial management systems, and more specifically, to identifying implied criteria for a clinical trial based on criteria explicitly identified in similar clinical trials.

Clinical trials in medicine are research studies that are used to test and evaluate various medical treatments, drugs, or devices under development. Typically, clinical trials are defined as a treatment, drug, or device being developed, eligibility criteria (or inclusion criteria) defining the characteristics of patients who may be eligible to participate in a specified trial, and disqualifying criteria defining the characteristics of patients who are not eligible for participation in the trial. For example, the eligibility criteria may include the medical condition that the subject of the clinical trial is addressing, a stage of medical treatment that patients should be at, what previous treatments a patient may have received prior to entering the clinical trial, and the like. The disqualifying criteria defining the characteristics of patients who are not eligible to participate in a specified trial may include, for example, a stage of a disease beyond which a patient would be ineligible for inclusion in the trial, previous treatments that disqualify a patient from participating in the trial, and the like. While clinical trial eligibility and disqualifying criteria may be written according to a standard format, the eligibility and disqualifying criteria and other relevant information about clinical trials may not be written in a clear and concise manner.

At any given time, a patient may potentially be eligible for participation in a variety of clinical trials. Typically, to determine what clinical trial(s) a patient may be eligible for participation in, the patient's doctors and/or other clinical staff may review the patient's medical records and the eligibility and disqualifying criteria for a number of clinical trials to identify trials that may be of interest to the patient. However, the process of identifying trials that are potentially of interest for the patient may be a time consuming, manual process that requires doctors or other clinical staff to compare potentially voluminous patient records with at least the eligibility and disqualifying criteria for each clinical trial. Further, due to the number and wide variety of clinical trials that may be active at any time, manual searches for trials of interest may miss potentially relevant trials for a given patient. In some cases, manual analysis of potential clinical trials to enroll a patient in may rely on institutional procedures that prioritize clinical trials being run in certain institutions over potentially relevant clinical trials run in other institutions, which may result in potentially relevant clinical trials for a patient being overlooked or otherwise omitted from consideration.

Automated methods for analyzing patient records and clinical trial definitions may not be able to accurately match patients with the clinical trials that patients may be eligible to participate in for various reasons. For example, automated methods may not be able to accurately parse the intent of statements in a clinical trial definition. In another example, automated methods may not be able to understand the implications of a patient's records with respect to the ability to successfully complete a clinical trial. In still further examples, automated methods may be unable to determine or identify temporal relationships associated with eligibility or disqualifying criteria for a clinical trial.

SUMMARY

One embodiment of the present disclosure provides a method for identifying implied criteria for a clinical trial based on criteria defined for other clinical trials. The method generally includes generating a training data set from a corpus of clinical trial specifications. The training data set may include at least a first sample corresponding to a first trial. The first sample may include a first feature based on one or more explicitly stated trial criteria, a second feature based on metadata describing the first trial, and a third feature based on patient data of patients associated with the first trial. A machine learning model is trained, using a supervised learning approach, based on the training data set. A system processes a second trial as an input to the trained machine learning model to determine one or more implied criteria that are not explicitly enumerated in a specification for the second trial.

Another embodiment of the present disclosure provides a system having a processor and a memory. The memory generally has instructions stored thereon which, when executed by the processor, performs an operation for identifying implied criteria for a clinical trial based on criteria defined for other clinical trials. The operation generally includes generating a training data set from a corpus of clinical trial specifications. The training data set may include at least a first sample corresponding to a first trial. The first sample may include a first feature based on one or more explicitly stated trial criteria, a second feature based on metadata describing the first trial, and a third feature based on patient data of patients associated with the first trial. A machine learning model is trained, using a supervised learning approach, based on the training data set. A system processes a second trial as an input to the trained machine learning model to determine one or more implied criteria that are not explicitly enumerated in a specification for the second trial.

Still another embodiment of the present disclosure provides a computer-readable medium having instructions stored thereon which, when executed by a processor, performs an operation for identifying implied criteria for a clinical trial based on criteria defined for other clinical trials. The operation generally includes generating a training data set from a corpus of clinical trial specifications. The training data set may include at least a first sample corresponding to a first trial. The first sample may include a first feature based on one or more explicitly stated trial criteria, a second feature based on metadata describing the first trial, and a third feature based on patient data of patients associated with the first trial. A machine learning model is trained, using a supervised learning approach, based on the training data set. A system processes a second trial as an input to the trained machine learning model to determine one or more implied criteria that are not explicitly enumerated in a specification for the second trial.

DETAILED DESCRIPTION

Figure 1:
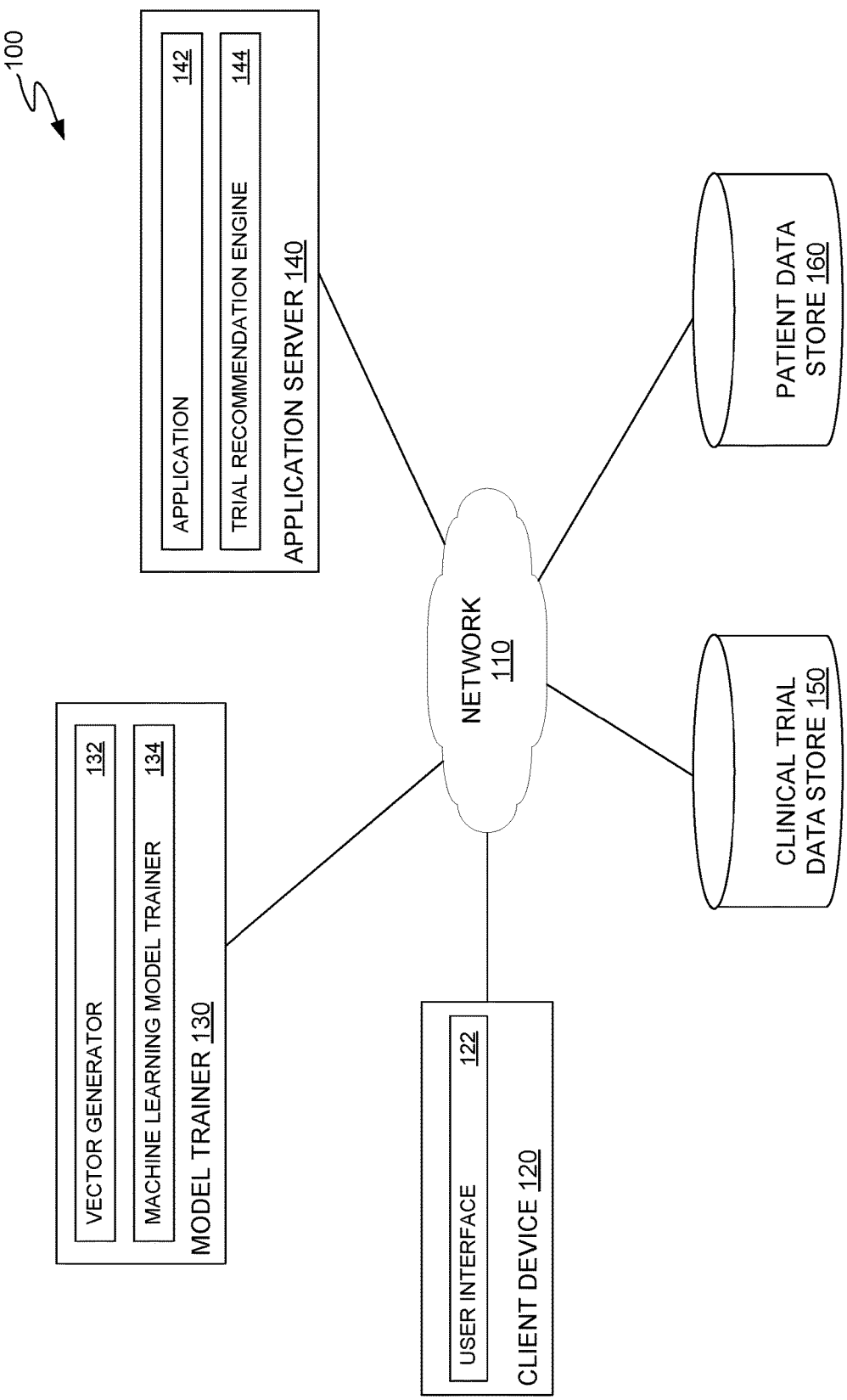
FIG. 1 illustrates an example networked environment in which machine learning models are used to predict intended respondents and timing for evaluating clinical trial eligibility for a patient, according to one embodiment.

Embodiments presented herein describe techniques for identifying implied criteria for a clinical trial using machine learning techniques. As discussed, clinical trials are generally defined by eligibility criteria, which indicates which patients may be enrolled into a trial, and disqualifying criteria, which are conditions, previous treatments, etc. that prevent patients from being enrolled into the trial. However, clinical trial specifications may not be written clearly and may lack detail, leading to ambiguities in identifying what the eligibility and disqualifying criteria are and thus difficulty in understanding whether a patient is eligible to participate in a specific clinical trial. Additionally, clinical trial specifications may omit trial criteria. Such omissions may be inadvertent or may be the result of trial investigators assuming that clinicians would be able to fill in such criteria. For example, a clinical trial may investigate a particular pharmaceutical agent for the treatment of a given medical condition but may not include information about other medications that would disqualify a patient from participating in a trial if the patient were prescribed those medications (e.g., medications that have known contraindications with the pharmaceutical agent under investigation). In another example, a pharmaceutical agent may be known to have adverse effects, though the clinical trial specification may not include criteria related to the adverse effects (e.g., where a pharmaceutical agent is known to have adverse effects on an organ, implied criteria not included in the clinical specification may include disqualifying criteria for patients with insufficient organ function). Because these criteria may be implied, but not explicitly identified, in a clinical trial specification, automated methods of determining whether a patient is eligible for participation in a clinical trial may result in the inclusion of clinical trials that the patient is ineligible for participation in, in a recommended set of clinical trials for the patient.

As discussed herein, embodiments of the present disclosure use intelligent analyses of clinical trials to identify implied, but not explicitly listed, criteria in a clinical trial specification using machine learning models trained using training data sets of clinical trials. By inferring the existence of unlisted criteria in a clinical trial specification based on criteria in other clinical trials, embodiments of the present disclosure can augment clinical trial specifications with additional information that may be used as part of a search and/or filtering process to identify potentially relevant clinical trials that a patient may be eligible to participate in. The addition of implied criteria to a clinical trial specification may be used, in conjunction with patient medical information, to identify potentially relevant clinical trials that a patient is ineligible for participation in and remove those trials from a set of potentially relevant clinical trials returned to a user of a clinical trial management system, which may reduce the rate at which false positives are included in recommended sets of clinical trials.

FIG. 1 illustrates an example networked computing environment in which machine learning models are used to identify who should provide information about clinical trial eligibility and disqualifying criteria and when such information should be provided, according to an embodiment of the present disclosure. As illustrated, computing environment 100 includes a client device 120, a model trainer 130, an application server 140, a clinical trial data store 150, and a patient data store 160, connected via network 110.

Client device 120 generally is representative of a computing device on which a user can define and/or manage the training of predictive models used by trial recommendation engine 144 to recommend potentially relevant clinical trials for a patent and access application 142 on application server 140 to obtain a set of potentially relevant clinical trials for a patient and analyze eligibility and disqualifying criteria for one or more trials in the set of potentially relevant clinical trials. Client device 120 may be, for example, a laptop computer, a desktop computer, a thin client, a tablet computer, a mobile computing device, and the like. As illustrated, client device 120 includes a user interface 122. User interface 122 allows a user of client device 120 to define a training data set for use in training machine learning models for identifying eligibility and disqualifying criteria in a clinical trial, classes of persons qualified to provide information about each of the eligibility and disqualifying criteria, and timing information identifying when information should be provided about each of the eligibility and disqualifying criteria. User interface 122 additionally allows a user of client device 120 to initiate a search for recommended clinical trials that may be of interest to a patient by providing, to application 142, the patient's medical records in a request for one or more potentially relevant clinical trials to present to a patient. For each of the one or more potentially relevant clinical trials returned by application 142 on application server 140, the eligibility and disqualifying criteria as well as information generated by a machine learning model identifying who should provide information about clinical trial eligibility and disqualifying criteria and when such information should be provided may be displayed to a user for further analysis.

Model trainer 130 generally uses information about patients previously enrolled in trials and the criteria defined for those trials to train one or more machine learning models used in recommending clinical trials that are potentially relevant to a particular patient and identifying contextual information for one or more of the recommended clinical trials. As discussed, the contextual information may include, without limitation, who should provide information about clinical trial eligibility and disqualifying criteria, when such information should be provided, and preconditions that must be satisfied in order to provide information about clinical trial eligibility and disqualifying criteria. As illustrated, model trainer 130 includes a vector generator 132 and a machine learning model trainer 134.

Vector generator 132 is generally configured to generate a training data set for use by machine learning model trainer 134 to train a machine learning model for recommending potentially relevant clinical trials to a user based on patient medical history. To generate the training data set, vector generator 132 can obtain information about previously completed from clinical trial data store 150 and patient medical history data from patient data store 160. The information obtained from clinical trial data store 150 may include, for example, a roster of patients enrolled in a specific clinical trial and a definition of that clinical trial. The definition of the clinical trial may include eligibility and disqualifying criteria, patient requirements for participation in the trial, a trial enrollment deadline, and other information defining the clinical trial. The roster of patients may include information identifying each patient that vector generator 132 can use to obtain patient medical records from patient data store 160.

To generate the training data to be used by clinical trial recommendation trainer 134, vector generator can generate a first set of training data comprising feature data and label data used to train a machine learning model and a second set of unlabeled feature data that can be used to test the generated machine learning model. For example, in an embodiment where machine learning techniques are used to recommend relevant trials for a patient, the first set of data may comprise a plurality of vectors, where the features in each vector include information from patient medical records, and the labels in each vector include the characteristics of a given clinical trial (e.g., eligibility criteria and disqualifying criteria defined for a clinical trial). The second set of data may comprise an unlabeled set of patient medical records associated with patients who have been accepted into a clinical trial.

In some embodiments, the features in the first set of data may further include additional data that may be used to further refine recommendations of trials that may be relevant to a patient. This additional data may include, for example, information about a current stage of treatment that a patient is in, the specialty of the patient's clinicians, the institution that is treating the patient, and patient completion success for other trials that the patient may have participated in. These additional features may be used to further refine the recommendations delivered by trial recommendation engine 144 to deliver more relevant recommendations to the patient's doctors. For example, the use of information about a stage of treatment that the patient is in may be used to prioritize recommendations of trials relevant to that particular stage of treatment over trials relevant to earlier or later stages of treatment (e.g., where a patient is in an early stage of a disease, prioritizing clinical trials directed to curative treatments over palliative treatments that are more appropriate for patients with later or terminal stages of the disease). Likewise, using information about the patient's clinicians may further indicate, at least implicitly, relevant information about the patient's conditions, such as disease progression, that may be used to prioritize some clinical trials over others. This information may, for example, prioritize clinical trials being held at particular institutions (e.g., based on a distance metric from the patient's clinicians) based on assumptions that patients are more likely to successfully participate in trials that are more easily accessible to the patient. Finally, information about the patient's previous trial completion success may be used as an input to prioritize trials, for example, with similar or less stringent completion requirements to trials that the patient has previously successfully participated in. It should be noted, however, that these additional data points for refining the recommendation of relevant trials is not exhaustive, and other appropriate data points may be used to train predictive models for delivering recommendations of potentially relevant clinical trials for a given user.

In some embodiments, vector generator 132 may be further configured to generate a training data set for use in training a machine learning model to identify implied criteria in a clinical trial. To generate the training data set, vector generator 132 can extract clinical trial title and criteria information for one or more clinical trials stored in clinical trial data store 150. Vector generator 132 can generate a vector including the title of a clinical trial and/or other trial metadata (e.g., medical condition being treated, interventions being tested, etc.) as feature data and the one or more trial criteria as labels associated with the titles of the clinical trial. In some embodiments, the titles used as feature data for the vectors generated by vector generator 132 may be truncated to include, for example, information about a pharmaceutical agent under investigation, a medical procedure under investigation, or other information that may be probative of implied criteria in the clinical trial, such as contraindicated medications or procedures that may render a patient ineligible for participation in a clinical trial.

In some embodiments, vector generator 132 may augment the clinical trial specifications used to generate the training data set with additional information obtained from other data sources. For example, vector generator 132 can use one or more authoritative databases to identify contraindicated medications or procedures for a given intervention being tested in a clinical trial. If the clinical trial specification includes the contraindicated medications or procedures in disqualifying criteria, vector generator 132 need not take any action to augment the clinical trial specification. If, however, vector generator 132 determines that the clinical trial specification does not include the contraindicated medications or procedures in disqualifying criteria, vector generator 132 can take one or more actions to include the contraindicated medications or procedures in a vector generated for the clinical trial. These actions may include, for example, including the contraindicated medications and/or procedures as disqualifying criteria in the label data associated with the title or metadata of the clinical trial used as feature data in a vector in the training data set.

As discussed herein, the vectors generated by vector generator 132 for the first and second training data sets may be generated using a variety of techniques. In some embodiments, the vectors may be generated from a corpus of clinical trials using natural language processing (NLP) techniques such as the Bag of Words Model or Term Frequency and Inverse Document Frequency (TD-IDF) Model. Other NLP techniques, such as the word2vec algorithm or other neural network-based algorithms, may also be used to create vectors for the first and second training data sets. Additionally, key concepts, logical parse, key criterion triggers, and other non-NLP techniques may be used to generate vectors from corpuses of clinical trials. Criterion triggers may include, for example, hypothetical spans, negations, ignorable passages, and other criteria that may be used to identify relevant information in a clinical trial specification to be included in a vector.

Machine learning model trainer 134 generally is configured to obtain the training data generated by vector generator 132 and, using supervised learning techniques, train one or more predictive models for delivering recommendations of potentially relevant clinical trials for a patient.

In some embodiments, machine learning model trainer 134 may train a first machine learning model used to identify an initial set of clinical trials that are likely to be relevant to a patient based on patient medical data and the characteristics of each clinical trial (e.g., eligibility and exclusion criteria). To train the first machine learning model, recommendation engine trainer 134 can utilize supervised learning techniques using the first training data set discussed above. The labeled data in the first training data set may be used to initially train the first machine learning model, and a user may test the initially trained first machine learning model using the unlabeled data in the first training data set to verify that the first machine learning model returns accurate results (e.g., a recommended set of clinical trials including one or more trials that a patient actually enrolled in) and, if needed, further refine the trained machine learning model based on real-life clinical trial enrollment data associated with a given patient in the unlabeled data.

Further, machine learning model trainer 134 may be further configured to train a second machine learning model to identify implied criteria in a clinical trial using the training data set of clinical trial title and/or metadata information labeled with clinical trial criteria, as discussed above. Machine learning model trainer 134 may use supervised learning techniques to train the second machine learning model. The second machine learning model may be configured to receive, as input, information about an intervention to be tested in a clinical trial and receive as output information predicted eligibility and disqualifying criteria for the clinical trial. In some embodiments, the second machine learning model may return a probability distribution over a universe of eligibility and disqualifying criteria, where criteria with higher probability values are more likely to be relevant to the intervention to be tested in the clinical trial and criteria with lower probability values are less likely to be relevant to the intervention to be tested.

After training the second machine learning model, machine learning model trainer 134 may deploy the model for use by application 142 and/or trial recommendation engine 144, as described in further detail below. Generally, deployment of the model for use by application 142 may be performed when clinical trial specifications are being authored by trial investigators or when analysis of a clinical trial is to be performed on an on-demand basis (e.g., when a clinician is reviewing a set of recommended clinical trials to identify one or more trials that may benefit the patient). Deployment of the model for use by trial recommendation engine 144 may be performed when analysis of a clinical trial is to be performed as part of generating a recommended set of clinical trials (e.g., to exclude potentially relevant trials returned from execution of the first machine learning model that the patient would not be eligible to participate in). In some embodiments, the second machine learning model may be deployed as an independent application on application server 140 that is configured to aperiodically or periodically scan clinical trial data store 150 to identify trials that have been added to clinical trial data store 150 since the last scan and add implied criteria to the newly identified trials using the output of the second machine learning model.

In some embodiments, recurrent algorithms may be used to train the machine learning models described herein. Using recurrent algorithms, such as a Recurrent Neural Network (RNN), the machine learning models may be configured to return one or more values indicative of a likelihood, for example, that a particular clinical trial is relevant to a patient or that a particular implied criterion is applicable to a given clinical trial. Further, by using RNNs to train the machine learning models described herein, the machine learning models can analyze clinical trial specifications in the scope of continuous sequences, such as sentences or phrases in a clinical trial specification. In some embodiments, classification type algorithms, where the output of a trained machine learning model is an identified category, may also be used to identify types of clinical trials that a user may be eligible for participation in and implied criteria applicable to a given clinical trial.

Application server 140 generally includes an application 142 and a trial recommendation engine 144. Application 142 may be any type of application in which users can generate clinical trial specifications and/or request recommendations of potentially relevant clinical trials for a patient by providing patient data (e.g., medical condition information, treatment history, prior clinical trial participation history, and other relevant information) and, in some embodiments, user-defined filters in a search request executed by application 142. Client device 120 may instantiate or initiate a session of application 142 in response to a request for application content (e.g., a list of active clinical trials that are enrolling patients for participation) generated by a user of client device 120. In some embodiments, the instance of a session of application 142 may be instantiated by a user of client device 120 accessing a home page of an application 142 structured as a web application. In other embodiments, user interface 122 may instantiate the instance of application 142 by launching an executable file on client device that includes components that execute locally on client device 120 and use data provided by application 142.

During execution of application 142, a user may request a set of recommended clinical trials for a given patient by providing that patient's medical data to application 142 in conjunction with a search request. In response, application 142 provides the received medical data to trial recommendation engine 144 for analysis. Application 142 may receive a list of potentially relevant clinical trials for the patient from trial recommendation engine, as discussed in further detail below, and display the list of potentially relevant clinical trials in user interface 122 of client device 120. In some embodiments, the list of potentially relevant clinical trials may include a predetermined number of potentially relevant clinical trials for the patient and may be sorted based on the predictive scores associated with each of clinical trial in the list of potentially relevant clinical trials. Application 142 may additionally allow a user of client device 120 to further refine the list of potentially relevant clinical trials using one or more user-defined filters.

In some embodiments, application 142 may additionally be configured to aperiodically (e.g., upon user request) or periodically analyze sets of clinical trial specifications using the second machine learning model to augment clinical trial specifications with implied criteria that are not included in the clinical trial specifications but may be implied based on the title of a clinical trial or metadata related to the clinical trial. For example, the implied criteria may be generated by providing information about an intervention being tested by a clinical trial (which may be specified in one or both of the title of the clinical trial and the metadata associated with the clinical trial) to the second machine learning model generated by machine learning model trainer 134 and receiving a probability distribution over a set of possible criteria that may be included in a clinical trial specification. Application 142 can identify one or more probable criteria that should be included in the clinical trial specification based on the probability scores returned for these criteria being above a threshold probability score. For each criterion of the probable criteria, application 142 can examine the clinical trial specification to determine whether the criterion is included in the clinical trial specification and, if the criterion is not included application 142 can determine that the criterion is an implied but omitted criterion for the clinical trial. Based on this determination, application 142 may augment the clinical trial criteria to include the implied but omitted criterion in the eligibility or disqualifying criteria for the clinical trial.

In some embodiments, application 142 may be configured to pre-populate a clinical trial specification or recommend criteria for inclusion in a clinical trial specification while the clinical trial specification is being authored. To identify criteria for inclusion in the clinical trial specification, application 142 may request at least a title of the clinical trial and/or information about an intervention (e.g., pharmaceutical agent or medical procedure) being tested in the clinical trial. Application 142 may provide the requested information to the second machine learning model for analysis and receive a recommended set of clinical trial eligibility and/or disqualifying criteria for the clinical trial. The recommended set of criteria may, for example, comprise the criteria having the highest n probability scores out of a set of criteria or criteria having probability scores exceeding a threshold value. In some embodiments, application 142 may prepopulate a clinical trial specification with the recommended set of criteria, and an author of the clinical trial specification may modify the clinical trial specification (e.g., add additional trial eligibility and/or disqualifying criteria, remove recommended criteria, etc.) as appropriate.

Trial recommendation engine 144 uses the machine learning model generated by recommendation engine trainer using the first training data set to examine medical records for a given patient and recommend potentially relevant clinical trials for the patient to the patient's clinicians based, at least in part, on the patient's medical history. Techniques for doing so are described in U.S. Patent Application No. XX/XXX,XXX of Clark et al., filed XXXXX, 2019 and entitled "Intelligent Ranking of Trials for a Patient", the contents of which are herein incorporated by reference.

In some embodiments, trial recommendation engine 144 may examine each clinical trial in the set of recommended clinical trials in order to identify implied criteria for the trials in the set of recommended clinical trials and eliminate trials from the set that have implied criteria that disqualify the patient. For each clinical trial in the set of recommended clinical trials, trial recommendation engine 144 may input the title trial or other metadata into the second machine learning model and obtain, for example, a probability distribution indicating the criteria that are likely applicable to the clinical trial. As discussed, these criteria may be learned from the inclusion of such criteria in clinically similar trials (e.g., trials investigating similar pharmaceutical agents or other medical interventions). For implied criteria that are disqualifying criteria, such as contraindicated medication or medical procedures, trial recommendation engine 144 may examine the provided patient data to determine whether the patient satisfies the implied criteria (e.g., is prescribed a contraindicated medication or has undergone a contraindicated medical procedure). If the patient satisfies a disqualifying criteria, the patient may not be eligible for participation in the clinical trial. Thus, trial recommendation engine 144 may remove the clinical trial from the set of recommended clinical trials, which may return a more focused and relevant set of recommended clinical trials to a user of application 142.

While model trainer 130, application server 140, clinical trial data store 150, and patient data store 160 are illustrated as separate components in FIG. 1, it should be recognized that model trainer 130, application server 140, clinical trial data store 150, and patient data store 160 may be implemented on any number of computing systems, either as one or more standalone systems or in a distributed environment.

Figure 2:
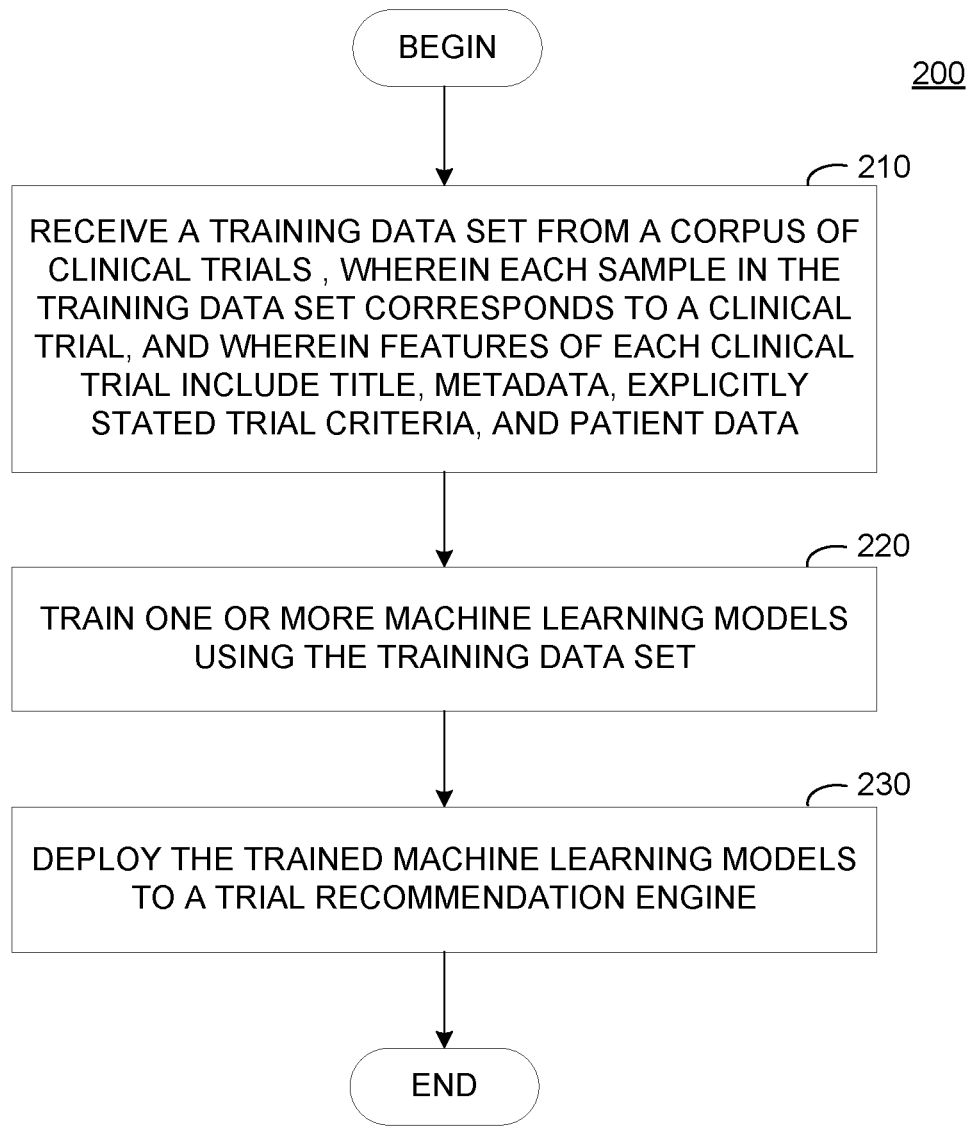
FIG. 2 illustrates example operations for training a machine learning model for predicting intended respondents and timing for evaluating clinical trial eligibility for a patient, according to one embodiment.

FIG. 2 illustrates example operations that may be performed by a machine learning model trainer to train a machine learning model for identifying implied criteria in a clinical trial, according to an embodiment.

As illustrated, operations 200 begin at block 210, where a system (e.g., model trainer 130 illustrated in FIG. 1) receives a training data set from a corpus of clinical trial specifications. In some embodiments, each sample in the training data set may correspond to a clinical trial. Each clinical trial may include a plurality of features, such as the title of the clinical trial, metadata defined for the clinical trial, explicitly stated trial criteria, patient data for patients enrolled in the trial, patient data for patients who were not accepted for the trial, and the like. In some embodiments, a sample in the training data set may be augmented with information sourced from one or more other data sources, such as pharmaceutical agent databases, medical data libraries, or other authoritative sources to include additional criteria in the sample. The training data set may be generated by a vector generator (e.g., vector generator 132 illustrated in FIG. 1) and provided to a machine learning model training engine or may be generated manually, stored in a data repository (e.g., clinical trial data store 150 illustrated in FIG. 1), and made available to a machine learning model training engine.

At block 220, the system trains a machine learning model based on the training data set. In some embodiments, the machine learning model may be trained using supervised learning techniques. The machine learning model may be trained to accept, as input, information about a clinical trial and return a recommendation or prediction of one or more trial criteria that are applicable to the clinical trial based on inferences made from the information about the clinical trial. The inferences may be based, for example, on attributes of clinically similar trials investigating the same or similar pharmaceutical agents or other medical interventions, as discussed above.

At block 230, the system deploys the trained machine learning model to application server 140 for use in identifying implied criteria in a clinical trial. As discussed in above, the identification of implied criteria using the trained machine learning model may be used to augment clinical trial specifications at authoring time, on demand, or as part of a trial recommendation system in which the identification of implied criteria may be used in conjunction with patient data to determine whether to include a clinical trial in a recommended set of clinical trials for a patient.

Figure 3:
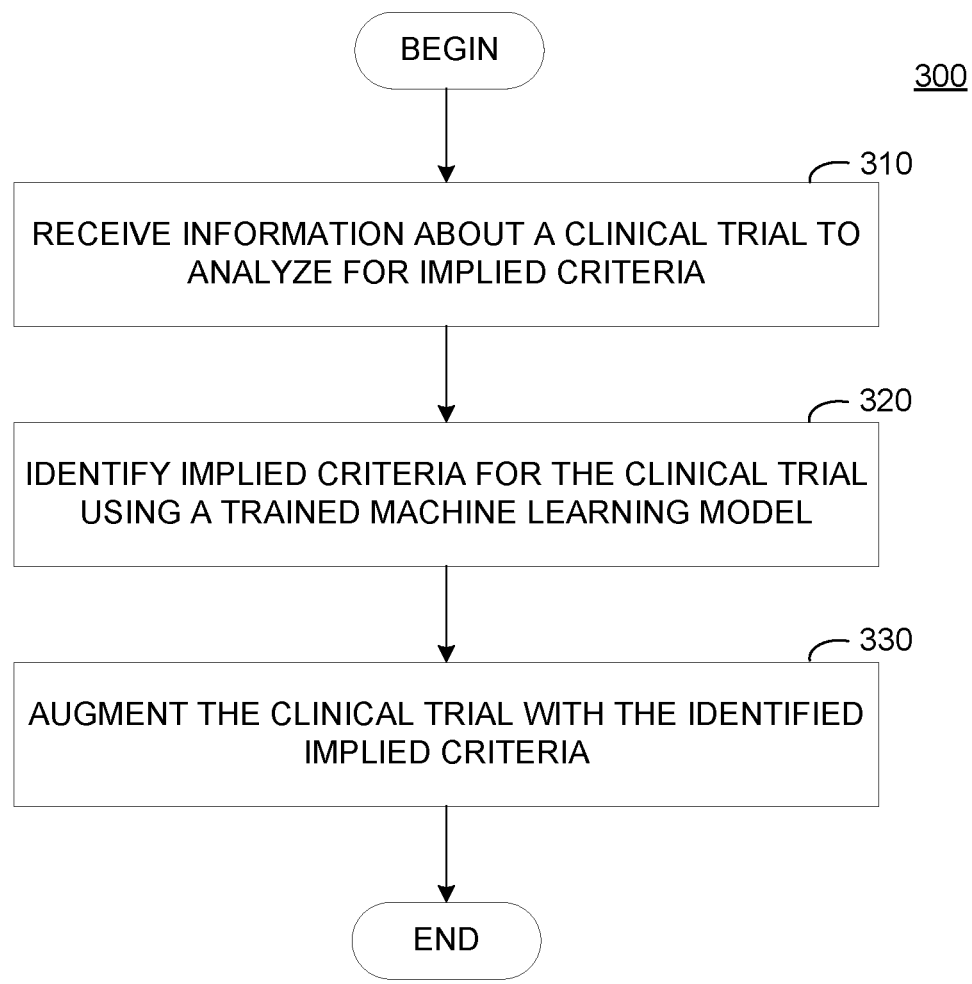
FIG. 3 illustrates example operations for predicting intended respondents and timing for evaluating clinical trial eligibility for a patient using a trained machine learning model, according to one embodiment.

FIG. 3 illustrates example operations that may be performed by a system for identifying implied criterial in a clinical trial using machine learning techniques, according to an embodiment.

As illustrated, operations 300 begin at block 310, where a system (e.g., application 142 illustrated in FIG. 1 and/or trial recommendation engine 144 illustrated in FIG. 1) receives information about a clinical trial to analyze for implied criteria. The system may receive the information about the clinical trial for analysis manually (e.g., when a trial investigator is creating a clinical trial specification, when a user views information about a recommended clinical trial, etc.) or during a process of identifying potentially relevant clinical trials for a patient to automatically eliminate irrelevant trials (e.g., trials that the patient is ineligible for participation in). In some embodiments, the information about the clinical trial received for analysis may include information about a pharmaceutical agent under investigation, a medical intervention (e.g., surgical procedure) under investigation, or other information that may be relevant to the determination of implied criteria for a clinical trial.

At block 320, the system identifies implied criteria for the clinical trial by analyzing the received information about the clinical trial through a trained machine learning model. To identify the implied criteria for the clinical trial, key characteristics can be identified about a criterion which may trigger a machine learning model to identify one or more implied criteria previously trained. For example, variations of the clinical trial criterion "pregnant or nursing" may be used to train a machine learning model to identify an implied criteria of "patient is female." When criteria for a clinical trial are evaluated, the identification of the words "pregnant" and/or "nursing" may serve as a trigger for identifying "patient is female" as an implied criteria for the clinical trial based on the responses learned previously. In some embodiments, the trained machine learning model may be used to generate a probability distribution over a universe of clinical trial eligibility and/or disqualifying criteria, where criteria with higher probability scores are more likely to be included in the clinical trial than criteria with lower probability scores. Based on the probability distribution, the system can identify a set of probable criteria that are likely to be applicable to the clinical trial (e.g., the n criteria with the highest probability scores, criteria with probability scores above a threshold value, etc.) and determine whether the probable criteria are included in the clinical trial specification. Probable criteria not included in the clinical trial specification may be identified as implied criteria.

At block 330, the system augments the clinical trial with the identified one or more implied criteria. In some embodiments, the system may add the identified one or more implied criteria to the clinical trial specification in clinical trial data store 150. In other embodiments, such as when implied criteria are identified as part of a trial recommendation process, the implied criteria may be added to a clinical trial specification in a temporary data store (e.g., random access memory, temporary storage, etc.). The implied criteria may be used in conjunction with the explicitly specified criteria in a clinical trial specification to determine whether a patient is eligible for participation in a clinical trial. If the patient is ineligible for participation in the clinical trial, the clinical trial may be excluded from a recommended set of clinical trials for the patient.

Figure 4:
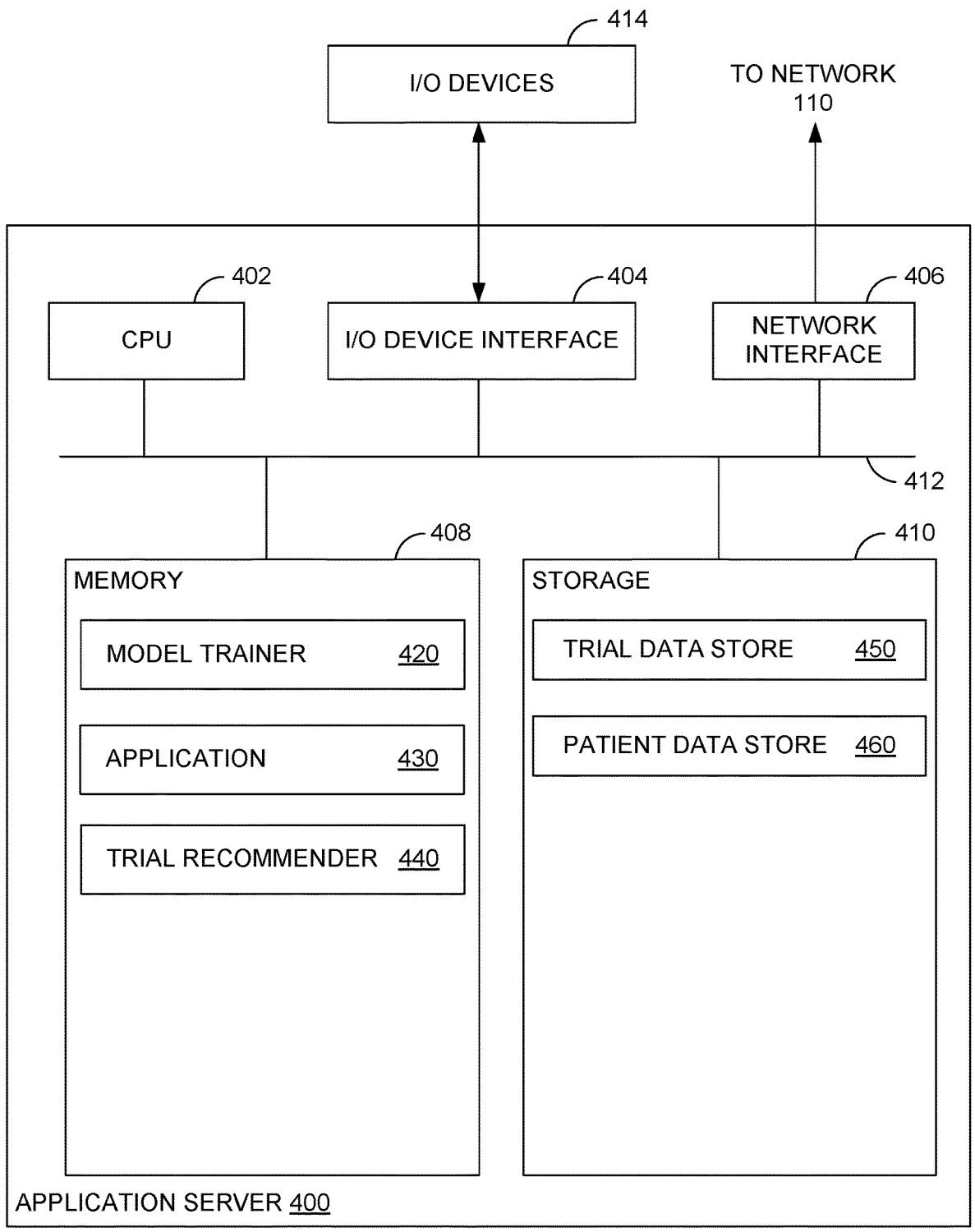
FIG. 4 illustrates an example system in which aspects of the present disclosure may be performed.

FIG. 4 illustrates an example application server 400 that uses machine learning techniques to identify implied criteria for a clinical trial, according to an embodiment. As shown, application server 400 includes, without limitation, a central processing unit 402, one or more I/O device interfaces 404, which may allow for the connection of various I/O devices 414 (e.g., keyboards, displays, mouse devices, pen input, etc.) to the entity analytics system 400, network interface 406, a memory 408, storage 410, and an interconnect 412.

CPU 402 may retrieve and execute programming instructions stored in the memory 408. Similarly, the CPU 402 may retrieve and store application residing in the memory 408. The interconnect 412 transmits programming instructions and application data among the CPU 402, I/O device interface 404, network interface 406, memory 408, and storage 410. CPU 402 is included to be representative of a single CPU, multiple CPUs, a single CPU having multiple processing cores, and the like. Additionally, the memory 408 is included to be representative of a random access memory. Furthermore, the storage 410 may be a disk drive. Although shown as a single unit, the storage 410 may be a combination of fixed and/or removable storage devices, such as fixed disc drives, solid state drives, removable memory cards or optical storage, network attached storage (NAS), or a storage area-network (SAN).

As illustrated, memory 408 includes a model trainer 420, an application 430, and a trial recommender 440. Model trainer 420 is generally configured to receive one or more training data sets of clinical trials for use in training one or more machine learning models. Each clinical trial in the training data sets may include a plurality of criteria, and each criterion may be labeled with contextual information identifying, for example, the intended respondent for the criterion, the intended time for responding to the criterion, preconditions for responding to the criterion, and the like. Model trainer 420 uses the received one or more training data sets to generate and deploy one or more machine learning models to application 430 and/or trial recommender 440 for use in identifying implied criteria for a clinical trial. In some embodiments, the one or more machine learning models may be used to control how a user interacts with application 430 in evaluating patient eligibility for a clinical trial and/or whether clinical trials are included in a recommended set of clinical trials for a patient.

Application 430 may be configured to periodically or aperiodically analyze clinical trial specifications to identify implied criteria for a clinical trial and augment the clinical trial specifications with the identified implied criteria. Generally, application 430 provides information about a clinical trial, such as the title of a trial, the intervention being tested, or other trial metadata, as input into the one or more machine learning models. The one or more machine learning models can identify implied criteria for the clinical trial based on learned criteria from clinically similar trials (e.g., trials considering the same or similar intervention being tested) and write the identified implied criteria to the clinical trial specification for future use. In some embodiments, application 430 may present a selected, augmented, clinical trial specification to a user of application 430 and use the identified implied criteria to assist a user in determining whether a patient is eligible for participation in a trial, as discussed above. In some embodiments, the identification of implied criteria for a clinical trial may be used at authoring time for clinical trial specifications to recommend a set of clinical trial criteria (e.g., eligibility and disqualifying criteria) that may be relevant for the clinical trial.

Trial recommender 440 is generally configured to receive patient data as input and generate a set of recommended clinical trials for the patient for display to a user of application 430. The set of recommended clinical trials may be generated using a model that compares the received patient data to other clinically similar patients who have previously participated in clinical trials and identifies clinically similar trials to the trials that the clinically similar patients have participated in. In some embodiments, trial recommender 440 may use the one or more machine learning models to augment the set of recommended clinical trials with implied criteria that is not explicitly stated in the specifications for the set of recommended clinical trials. Using the implied criteria, the explicitly stated criteria, and patient medical data provided to trial recommender 440, trial recommender 440 can determine whether a patient is ineligible for participation in a clinical trial. If trial recommender 440 determines that a patient is ineligible for participation in a clinical trial included in the set of recommended clinical trials, the clinical trial may be removed from the set of recommended clinical trials, thus reducing the number of false positives returned to a user of application 430 for further evaluation.

Storage 410, as illustrated, includes trial data store 450 and patient data store 460. Trial data store 450 generally represents a data repository in which details of previously performed and currently enrolling clinical trials are stored. Each trial stored in trial data store 450 generally includes eligibility and disqualifying criteria for the trial, operational characteristics of the trial, and the like. Patient data store 460 generally stores information about patients enrolled in previously performed trials and information about patients currently under consideration for inclusion in one or more clinical trials. As discussed, the patient information may be used to generate training data sets that are used to train machine learning models to recommend clinical trials for a patient.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method, comprising:
   generating a first training data set from a corpus of patient data, each sample in the first training data set mapping information from a patient medical record associated with a patient in the corpus of patient data to characteristics of one or more clinical trials for which the patient was enrolled;
   training a first machine learning model to identify a set of relevant clinical trials for a first user based on patient data of the first user;
   generating a second training data set from a corpus of clinical trial specifications, wherein a first training sample in the second training data set corresponds to a first trial, and wherein the first training sample comprises a first feature based on one or more explicitly stated trial criteria, a second feature based on metadata describing the first trial and a third feature based on patient data of patients associated with the first trial;
   training a second machine learning model, using a supervised learning approach, based on the training data set, to identify one or more implied criteria for a trial from an input of explicitly stated trial criteria and trial metadata, wherein the implied criteria comprise criteria that are not explicitly enumerated by a specification of the trial;
   receiving a request for a recommended set of clinical trials based on patient data of the first user;
   generating, using the first machine learning model and the patient data of the first user as input into the first machine learning model, a set of relevant trials for the first user;
   for each respective trial in the set of relevant trials for the first user:
      identifying, using the second machine learning model and a specification associated with the respective trial as an input to the trained machine learning model, one or more implied criteria that are not explicitly enumerated by the respective trial, and
      augmenting the specification associated with the respective trial by adding the identified one or more implied criteria identified using the second machine learning model to the specification associated with the respective trial;
   modifying the set of relevant trials for the first user by determining, for each respective trial in the set of trials, whether the first user qualifies for the respective trial based on the patient data, explicit criteria in the specification associated with the respective trial, and the one or more implied criteria and removing trials from the set of relevant trials for which the first user disqualified from participation based on a mismatch between the one or more implied criteria and the patient data for the first user; and
   recommending one or more trials from the modified set of relevant trials for the first user.

2. The method of claim 1, wherein the metadata describing the first trial includes a title of the first trial.

3. The method of claim 1, wherein the one or more explicitly stated trial criteria represent criteria that must be satisfied by trial participants in order for the trial participants to qualify for the first trial.

4. The method of claim 1, further comprising:
   determining that a first user does not qualify for the second trial, based on the one or more implied criteria, wherein the first user satisfies all explicitly enumerated criteria for the second trial.

5. The method of claim 1, wherein the patient data further comprises at least one of:
   patient data of patients who did qualify for the first trial, or
   patient data of patients who did not qualify for the first trial.

6. The method of claim 1, wherein generating the recommended set of clinical trials comprises:
   determining that the first user does not qualify for the respective trial based on the one or more implied criteria; and
   removing the respective trial from the recommended set of clinical trials.

7. A system, comprising:
   a processor; and
   a memory having instructions stored thereon which, when executed by the processor, perform an operation, the operation comprising:
      generating a first training data set from a corpus of patient data, each sample in the first training data set mapping information from a patient medical record associated with a patient in the corpus of patient data to characteristics of one or more clinical trials for which the patient was enrolled;
      training a first machine learning model to identify a set of relevant clinical trials for a first user based on patient data of the first user;

generating a second training data set from a corpus of clinical trial specifications, wherein a first training sample in the second training data set corresponds to a first trial, and wherein the first training sample comprises a first feature based on one or more explicitly stated trial criteria, a second feature based on metadata describing the first trial and a third feature based on patient data of patients associated with the first trial;

training a second machine learning model, using a supervised learning approach, based on the training data set, to identify one or more implied criteria for a trial from an input of explicitly stated trial criteria and trial metadata, wherein the implied criteria comprise criteria that are not explicitly enumerated by a specification of the trial;

receiving a request for a recommended set of clinical trials based on patient data of the first user;

generating, using the first machine learning model and the patient data of the first user as input into the first machine learning model, a set of relevant trials for the first user;

for each respective trial in the set of relevant trials for the first user:
identifying, using the second machine learning model and a specification associated with the respective trial as an input to the trained machine learning model, one or more implied criteria that are not explicitly enumerated by the respective trial, and augmenting the specification associated with the respective trial by adding the identified one or more implied criteria identified using the second machine learning model to the specification associated with the respective trial;

modifying the set of relevant trials for the first user by determining, for each respective trial in the set of trials, whether the first user qualifies for the respective trial based on the patient data, explicit criteria in the specification associated with the respective trial, and the one or more implied criteria and removing trials from the set of relevant trials for which the first user disqualified from participation based on a mismatch between the one or more implied criteria and the patient data for the first user; and recommending one or more trials from the modified set of relevant trials for the first user.

8. The system of claim 7, wherein the metadata describing the first trial includes a title of the first trial.

9. The system of claim 7, wherein the one or more explicitly stated trial criteria represent criteria that must be satisfied by trial participants in order for the trial participants to qualify for the first trial.

10. The system of claim 7, wherein the operation further comprises:
determining that a first user does not qualify for the second trial, based on the one or more implied criteria, wherein the first user satisfies all explicitly enumerated criteria for the second trial.

11. The system of claim 7, wherein the patient data further comprises at least one of:
patient data of patients who did qualify for the first trial, or
patient data of patients who did not qualify for the first trial.

12. The system of claim 7, wherein generating the recommended set of clinical trials comprises:

determining that the first user does not qualify for the respective trial based on the one or more implied criteria; and
removing the respective trial from the recommended set of clinical trials.

13. A non-transitory computer-readable medium having instructions stored thereon which, when executed by a processor, performs an operation, the operation comprising:
generating a first training data set from a corpus of patient data, each sample in the first training data set mapping information from a patient medical record associated with a patient in the corpus of patient data to characteristics of one or more clinical trials for which the patient was enrolled;

training a first machine learning model to identify a set of relevant clinical trials for a first user based on patient data of the first user;

generating a second training data set from a corpus of clinical trial specifications, wherein a first training sample in the second training data set corresponds to a first trial, and wherein the first training sample comprises a first feature based on one or more explicitly stated trial criteria, a second feature based on metadata describing the first trial and a third feature based on patient data of patients associated with the first trial;

training a second machine learning model, using a supervised learning approach, based on the training data set, to identify one or more implied criteria for a trial from an input of explicitly stated trial criteria and trial metadata, wherein the implied criteria comprise criteria that are not explicitly enumerated by a specification of the trial;

receiving a request for a recommended set of clinical trials based on patient data of the first user;

generating, using the first machine learning model and the patient data of the first user as input into the first machine learning model, a set of relevant trials for the first user;

for each respective trial in the set of relevant trials for the first user:
identifying, using the second machine learning model and a specification associated with the respective trial as an input to the trained machine learning model, one or more implied criteria that are not explicitly enumerated by the respective trial, and augmenting the specification associated with the respective trial by adding the identified one or more implied criteria identified using the second machine learning model to the specification associated with the respective trial;

modifying the set of relevant trials for the first user by determining, for each respective trial in the set of trials, whether the first user qualifies for the respective trial based on the patient data, explicit criteria in the specification associated with the respective trial, and the one or more implied criteria and removing trials from the set of relevant trials for which the first user disqualified from participation based on a mismatch between the one or more implied criteria and the patient data for the first user; and recommending one or more trials from the modified set of relevant trials for the first user.

14. The non-transitory computer-readable medium of claim 13, wherein the operation further comprises:
determining that a first user does not qualify for the second trial, based on the one or more implied criteria, wherein the first user satisfies all explicitly enumerated criteria for the second trial.

15. The non-transitory computer-readable medium of claim 13, wherein generating the recommended set of clinical trials comprises:
   determining that the first user does not qualify for the respective trial based on the one or more implied criteria; and
   removing the respective trial from the recommended set of clinical trials.

16. The method of claim 1, wherein the one or more implied criteria comprise criteria derived from information about patients who qualified for trials in the training data set and patients who did not qualify for trials in the training data set.

17. The method of claim 1, wherein the one or more implied criteria comprise criteria derived from one or more authoritative data sources for an explicitly stated criteria in the specification associated with the respective trial.

18. The system of claim 7, wherein the one or more implied criteria comprise criteria derived from information about patients who qualified for trials in the training data set and patients who did not qualify for trials in the training data set.

19. The system of claim 7, wherein the one or more implied criteria comprise criteria derived from one or more authoritative data sources for an explicitly stated criteria in the specification associated with the respective trial.

20. The non-transitory computer-readable medium of claim 13, wherein the one or more implied criteria comprise criteria derived from one or more authoritative data sources for an explicitly stated criteria in the specification associated with the respective trial.

* * * * *